US010441897B2

(12) United States Patent
Tanskanen et al.

(10) Patent No.: US 10,441,897 B2
(45) Date of Patent: Oct. 15, 2019

(54) PROCESS SYSTEM FOR SEPARATING CHEMICALS, DISTILLATION COLUMN ARRANGEMENT, AND METHOD OF SEPARATING CHEMICALS

(71) Applicant: Chempolis Oy, Oulu (FI)

(72) Inventors: Juha Tanskanen, Oulu (FI); Werner Marcelo Goldmann Valdes, Oulu (FI)

(73) Assignee: Chempolis Oy, Oulu (FI)

( * ) Notice: Subject to any disclaimer, the term of this patent is extended or adjusted under 35 U.S.C. 154(b) by 734 days.

(21) Appl. No.: 14/973,266

(22) Filed: Dec. 17, 2015

(65) Prior Publication Data

US 2016/0175735 A1 Jun. 23, 2016

(30) Foreign Application Priority Data

Dec. 23, 2014 (FI) .................................. 20146147

(51) Int. Cl.
| | |
|---|---|
| *B01D 3/40* | (2006.01) |
| *B01D 3/00* | (2006.01) |
| *B01D 3/36* | (2006.01) |
| *C07C 51/46* | (2006.01) |
| *B01D 3/14* | (2006.01) |
| *C07C 67/327* | (2006.01) |

(52) U.S. Cl.
CPC ............. *B01D 3/40* (2013.01); *B01D 3/009* (2013.01); *B01D 3/143* (2013.01); *B01D 3/36* (2013.01); *C07C 51/46* (2013.01); *C07C 67/327* (2013.01); *Y02P 20/127* (2015.11)

(58) Field of Classification Search
CPC . B01D 3/40; B01D 3/009; B01D 3/36; B01D 3/143; C07C 51/46; C07C 67/327; C07C 7/04; C07C 53/02; Y02P 20/127
See application file for complete search history.

(56) References Cited

U.S. PATENT DOCUMENTS 3,024,170 A * 3/1962 Othmer ................... C07C 51/46
159/DIG. 19
3,394,058 A * 7/1968 Hoheuschutz ................. 203/15
(Continued)

FOREIGN PATENT DOCUMENTS

| FI | 117633 B | 12/2006 |
| JP | H10114699 A | 5/1998 |

OTHER PUBLICATIONS

National Board of Patents and Registration of Finland, Search Report for Application No. 20146147, dated Aug. 21, 2015, 2 pages, Finland.

*Primary Examiner* — Patrick Orme
(74) *Attorney, Agent, or Firm* — Alston & Bird LLP

(57) ABSTRACT

An arrangement for separating chemicals comprises a first distillation column (100) and the first distillation column (100) receives a mixture that comprises water and at least two organic acids and extractant that comprises at least one of the following: hexanol, an ester of hexanol with said at least one organic acid and 2-methylpentanol. The first distillation column (100) forms a heterogeneous azeotrope of water and extractant at its top (104) on the basis of reactive heteroazeotropic extractive distillation not controlling chemical reactions between the extractant and said at least two organic acids, said first distillation column (100) removing the azeotrope through its top (104) for separating water from the organic acid.

27 Claims, 3 Drawing Sheets

(56) References Cited

U.S. PATENT DOCUMENTS

| | | | |
|---|---|---|---|
| 5,160,412 A | 11/1992 | Berg | |
| 5,662,780 A | 9/1997 | Sasaki et al. | |
| 6,955,743 B2 * | 10/2005 | Rousu | D21C 3/04 |
| | | | 159/47.3 |
| 2004/0040830 A1 * | 3/2004 | Rousu | D21C 3/04 |
| | | | 203/1 |
| 2006/0047139 A1 * | 3/2006 | Ayoub | C07C 67/08 |
| | | | 560/155 |

* cited by examiner

PROCESS SYSTEM FOR SEPARATING CHEMICALS, DISTILLATION COLUMN ARRANGEMENT, AND METHOD OF SEPARATING CHEMICALS

CROSS-REFERENCE TO RELATED APPLICATIONS

This application claims priority to and the benefit of Finnish Patent Application Serial No. 20146147, filed Dec. 23, 2014, the contents of which as are hereby incorporated by reference in their entirety.

BACKGROUND

Technical Field

The invention relates to a process system for separating chemicals, a distillation column arrangement, and a method of separating chemicals.

Related Art

Distillation is a method commonly used in industry for separating substances dissolved in one another, based on different volatilities of the substances in a mixture. Distillation enables liquid substances dissolved in one another, as well as non-volatile and volatile substances to be separated.

Heteroazeotropic extractive distillation is an embodiment of distillation. A heteroazeotropic extractive distillation is described in Finnish Patent Publication FI 117633 B. In the method in question, a distillation step comprises utilizing the partial insolubility of water and furfural in one another, pressure dependence of azeotropes, extraction capacity of furfural as well as the binary azeotrope formed by furfural and water. In an azeotropic extraction method, the separation is implemented by a combination of azeotropic distillation and conventional extractive distillation. The method uses furfural simultaneously as both an extractant and an azeotrope forming agent for separating water from organic acids. Depending on the temperature, with water furfural forms either a homogeneous or heterogeneous azeotrope. In a temperature below 120° C., the azeotrope is heterogeneous, and therefore in a pressure range corresponding to this, extending from underpressure to moderate overpressure, the method is called heteroazeotropic extractive distillation. In the heteroazeotropic extractive distillation, the extractant has a double effect and generates two liquid phases, which enables the separation of water.

The safety classification for furfural used in the known solution has deteriorated in a REACH (Registration, Evaluation, Authorisation and Restriction of Chemicals) assessment. Further, when using an extractant, it is extremely important to control the mutual chemical reactions of the substances used in a process. At the same time, a need exists to separate chemicals in connection with an azeotropic extractive process, which is challenging as well.

BRIEF SUMMARY

An object of the invention is to provide an improved solution. This is achieved by a process system, a distillation column arrangement, and a method of separating chemicals according to the claims provided herein. Exemplary embodiments of the invention are disclosed in the dependent claims.

The apparatus and method according to the invention provide several advantages. As a non-limiting example an extractant security-classified as non-toxic may be used for separating chemical substances, which makes the process and the associated procedures simpler.

BRIEF DESCRIPTION OF THE SEVERAL VIEWS OF THE DRAWING(S)

The invention is now described in closer detail in connection with the preferred embodiments and with reference to the accompanying drawings, in which FIG. 1 shows an example of a process for separating chemical substances;

DETAILED DESCRIPTION OF VARIOUS EMBODIMENTS

The following embodiments are presented by way of example. Even though the description may refer to "an" embodiment or embodiments at different points, this does not necessarily mean that each such reference is made to the same embodiment or embodiments or that the feature only applies to one embodiment. Individual features of different embodiments may also be combined in order to enable other embodiments.

The expression "azeotrope" refers to a mixture of substances wherein vapour and liquid compositions are identical in a phase equilibrium. The azeotrope corresponds to an extreme point (minimum, maximum or saddle point) in a boiling temperature isobar or in a vapour pressure isotherm.

The expression "azeotropic distillation" refers to either distillation of azeotropic mixtures or distillation wherein an azeotrope forming component ("entrainer") is added to a process.

The expression "extractive distillation" refers to distillation wherein a fully soluble, azeotrope forming component ("entrainer") boiling at a relatively high temperature is added to a distillation column on top of the actual feed flow.

Extraction per se, again, refers to a process wherein a desired substance in a mixture dissolves in a solvent while the rest of the substances are insoluble in said solvent. In the mixture, the substances are completely mixed up with one another but the substances do not react chemically with one another in the mixture, even though the mixture per se may contain end products of chemical reactions.

The expression "heteroazeotrope" refers to an azeotrope having, in addition to the vapour phase, two liquid phases present.

The expression "heteroazeotropic distillation" refers to either distillation of heteroazeotropic mixtures or distillation wherein a heteroazeotrope forming component ("entrainer") is added to a process.

The expression "heteroazeotropic extractive distillation" refers to a combination of heteroazeotropic distillation and extractive distillation. The component to be added, boiling at a relatively high temperature, is selective and fully insoluble in one or more components in the mixture to be separated and boiling at a lower temperature, and it forms an azeotrope with any one of the remaining components.

The expression of "reactive distillation" (RD), a catalytic chemical reaction and distillation (fractionation of reactants and products) occur simultaneously in one single apparatus.

A column is a tubular, upright construction wherein substances fed thereto become completely mixed up together. Such a column may be used for separating different fluids from one another by means of a flow of the fluids. A typical field of application is chemical industry. The column per se is known to those skilled in the art.

Figure 1:
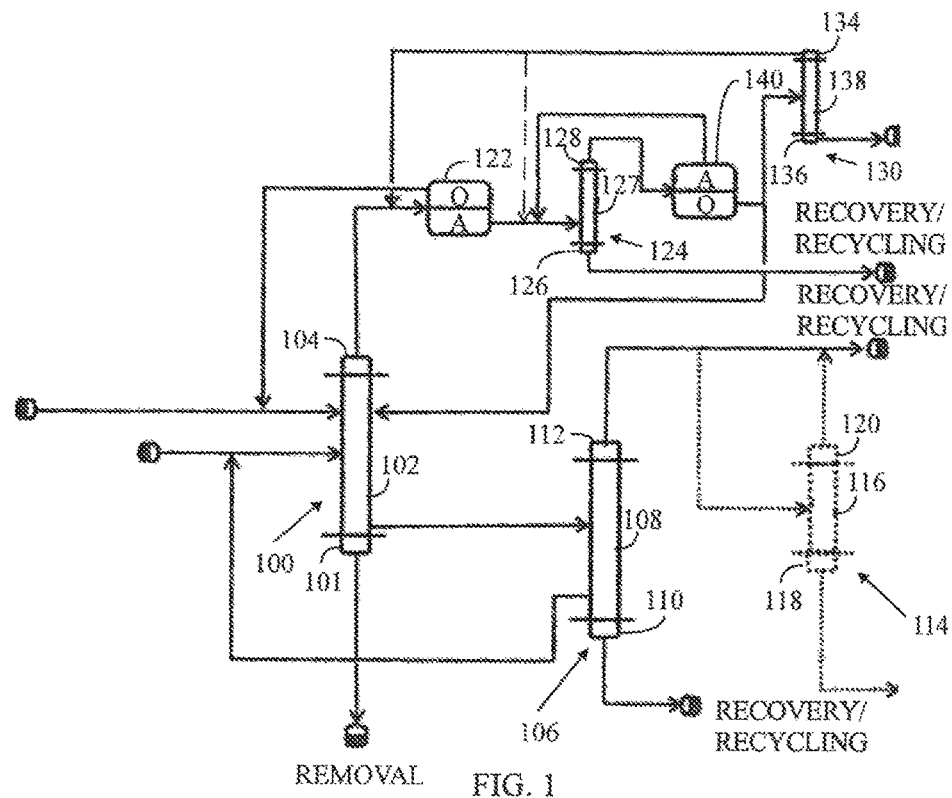

FIG. 1 shows an arrangement for separating chemicals, comprising a first distillation column 100 comprising at least one distillation condition. Columns are widely used in extraction and distillation, and herein the purpose of the distillation column 100 is to lower the water content of a feed by means of heteroazeotropic extractive distillation.

The first distillation column 100 receives a mixture comprising water and at least one organic acid, and at least one extractant. The organic acid may refer to one organic acid or more than one organic acid mixed together. The extractant may also refer to one extractant or more than one extractant mixed together. Said extractant comprises hexanol, an ester of hexanol with said at least one organic acid, and/or 2-methylpentanol. In this connection, hexanol also refers to n-hexanol. The first distillation column 100 receives the mixture and the one or more extractants via a side arrangement 102. The extractant may be fed to an upper part of the first distillation column 100. The side arrangement 102 generally refers to a side feed arrangement. The side feed arrangement may be a side inlet arrangement and/or a side outlet arrangement wherein the feed of the substance into the column or the feed of the substance out of the column takes place somewhere else than via a top or a bottom. The top is the uppermost part of the column while the bottom is the lowest part of the column.

The first distillation column 100 allows each of hexanol and/or 2-methylpentanol to react with said at least one organic acid in a manner not controlling the chemical reactions therebetween, in which case said freely occurring chemical reactions may produce reaction products. The extractant is thus allowed to react with one or more organic acids, to produce reaction products with these components, and these components are allowed to form an equilibrium mixture. Surprisingly, these reactions are equilibrium-restricted, and the state of the first distillation column 100 as a whole settles in a reaction equilibrium state according to the selected operating temperatures. For instance with hexanol, the organic acids produce esters. Surprisingly enough, however, the esters also act as extractants, which is why no reaction control is necessary. A mere one or more than one ester may thus also act as an extractant.

Even if hexanol, an ester of hexanol, and/or 2-methylpentanol is used as an extractant instead of furfural used in the prior art, the process produces the same chemicals and functions as a method based on furfural. The process thus further produces a mixed acid, water and an organic acid either to be used again in the process and/or to be sold as products in their own right.

When hexanol, an ester of hexanol, and/or 2-methylpentanol is used as an extractant, an advantage is for instance that the extractant is not classified as a toxic substance. Handling of toxic substances in connection with the process requires structural and operational special arrangements in order for those operating the process and the environment not to be exposed to these toxic substances, and this makes the process equipment and running of the process more complicated.

On the basis of reaction aided heteroazeotropic extractive distillation, the first distillation column 100 forms a heterogeneous azeotrope of water and extractant at its top 104, which azeotrope the first distillation column 100 removes through its top 104. Reaction aided heteroazeotropic extractive distillation may also be called reactive heteroazeotropic extractive distillation. The azeotrope boils at a lower temperature than any other substance component of the first distillation column 100, and the azeotrope ascends as a distillate out of the first distillation column 100.

In reactive distillation (RD), a catalytic chemical reaction and distillation (fractionation of reactants and products) occur simultaneously in one single apparatus. The reactive distillation belongs to the so-called "process-intensification technologies". From the reaction engineering view point, the process setup can be classified as a two-phase countercurrent fixed-bed catalytic reactor. This enables water to be separated from the organic acid, which will remain in the first distillation column 100, and transferred to further processes, recycling or the like. Since the mixture in question is an azeotrope, some extractant is also removed along with the water.

The first distillation column 100 may operate for instance in a pressure range of 0.2 bar to 2.5 bar. In an embodiment, the pressure is 1 bar. In an embodiment, the first distillation column 100 has a vacuum. In the first distillation column 100, the processing temperature may be 40° C. to 200° C., for example. Heavy and/or solid substances may be removed from a bottom 101 of the first distillation column. The substances removed from the bottom 101 may be destroyed, for instance.

In an embodiment, heavy components, which may be feed impurities, may be removed from the bottom 101 of the first distillation column 100.

In an embodiment, the organic acid comprises at least one of the following: formic acid and acetic acid. The ester serving as the extractant, formed upon these acids reacting with hexanol, may thus in this connection refer for instance to hexyl acetate formed for instance upon hexanol reacting with acetic acid, and to hexyl formate formed for instance upon hexanol reacting with formic acid.

For instance hexanol is allowed to react with formic acid and acetic acid and form esters with these components, as well as allow these components to form an equilibrium mixture. It was surprisingly discovered that the reactions between water, hexanol, hexyl acetate and hexyl formate are equilibrium-restricted, and the state of the first distillation column 100 as a whole settles in a reaction equilibrium state according to the selected operating temperatures.

In an embodiment, the composition to be fed to the first distillation column 100 may contain acetic acid about 12% by weight. In addition, the composition to be fed may contain about 40% of organic acids and about 60% of water (in the application all concentrations are given in percentages by mass). In an embodiment, the distillation column 100 may contain acetic acid and formic acid in equal amount. In an embodiment, the relative amount of acetic acid in the organic acids may be 10% or more. In an embodiment, the relative amount of acetic acid in the organic acids may be at most 60%.

In an embodiment, the arrangement comprises a third distillation column 106, the purpose of which is to separate an aqueous acid flow from an extractant mixture by conventional distillation so that the acid-containing flow may be returned back to the fractionation process. In this case, the first distillation column 100 may feed said at least one organic acid, extractant and water to the third distillation column 106. These substances may be transferred from one column to another via the side arrangement 102 of the first distillation column 100 and a side arrangement 108 of the third distillation column 106. There may be, for instance, 2 to 8% of water with the organic acid and the extractant. The third distillation column 106 may produce, by distillation, extractant on its bottom 110 for recovery and/or recycling. In addition, the third distillation column 106 may feed the extractant from its bottom 110 back to the first column 100. Azeotropic distillation is not applied in the third distillation column 106.

In an embodiment, on the basis of distillation, the third distillation column 106 may produce at its top 112 a mixture of water and said at least one organic acid, which may be recovered and/or recycled.

In an embodiment, the arrangement comprises a fourth distillation column 114, the purpose of which is to produce a pure organic acid from the distillate (the mixture of organic acids and water) of the third distillation column 106. At the bottom 118 of the fourth distillation column 114, the organic acid is concentrated. At the top 120 of the fourth distillation column 114, an acid-water mixture is formed, which may be returned to the fractionation process. Typically, only part of the flow at the top 112 of the third distillation column 106 is led to the fourth distillation column 114. The acid-water mixture comprises a mixture of water and said at least one organic acid.

The fourth distillation column 114 may thus receive the mixture of water and said at least one organic acid from the top 112 of the third distillation column 106. The reception may be performed via a side arrangement 116. The fourth distillation column 114 may produce, by distillation, at least one enriched organic acid on its bottom 118 for recovery and/or recycling. The fourth distillation column 114 may also form at its top 120 a mixture of water and said at least one organic acid for recovery and/or recycling. This makes the separation of the acid from the mixture more effective.

In an embodiment, the first distillation column 100 may also receive furfural via its side arrangement 102. The first distillation column 100 may remove aqueous furfural via its top 104.

In an embodiment, the arrangement comprises a first decanter 122. The purpose of the first decanter 122 is to divide a heteroazeotropic extractant water flow (n-hexanol/hexyl acetate/hexyl formate/2-methylpentanol water flow) into two liquid phases. The first decanter 122 may receive an azeotrope containing extractant and water at a temperature of 25 to 95° C.

The first distillation column 100 may thus feed the aqueous extractant produced as distillate via its top 104 to the first decanter 122, which separates the aqueous phase and the organic phase containing the extractant from one another. A decanter is a vessel separating different liquid phases mixed with each other from one another (for instance, two liquids from one another) or substances in two different states (for instance, particles of a liquid acting as a medium and a solid) from one another. The decanter is made of an inert material so that it would not have an effect on substances to be separated. The decanter may separate the mixed substances from one another by letting the mixture settle for a sufficiently long time and, as a result of different densities of the mixed substances, the substances are naturally separated from one another due to a different force caused by gravitational acceleration. The decanter may also comprise a centrifuge, by which a desired acceleration may be applied to the substances to be separated and the substances with different densities may thus be provided with a force of a desired magnitude, which makes it possible to separate the mixed substances from one another.

In the first decanter 122, the organic phase, which in this case is a substance less dense than water, rises to the top and the aqueous phase with a greater density remains at the bottom (the force causing acceleration being directed from the surface towards the bottom). The first decanter 122 may feed at least part of the organic phase back to the first distillation column 100 as extractant. The use of hexanol, an ester of hexanol, and/or 2-methylpentanol as extractant provides the advantage that, for example, water is separated more clearly in the first decanter 122. Esters can also be separated particularly well in the first decanter 122 and returned to the first distillation column 100.

In an embodiment, the arrangement comprises a fifth distillation column 124, the purpose of which is to separate water from the extractant mixture and to produce a clean water flow that is to be returned to the fractionation process (away from the distillery). The first decanter 122 may feed the aqueous phase to the fifth distillation column 124, which may produce, by distillation, water on its bottom 126 for recovery and/or recycling. A clean water flow is obtained from the bottom 126. In this way, water can be separated effectively from the acids.

In an embodiment, the fifth distillation column 124 may produce, by distillation, extractant at its top 128 and feed the extractant to a second decanter 140. The second decanter 140 may separate the aqueous phase and the organic phase containing extractant from one another. In the second decanter 140, the aqueous phase is in the surface and the organic phase on the bottom (the force causing acceleration being directed from the surface towards the bottom). The second decanter 140 may feed the aqueous phase back to the fifth distillation column 124 and the organic phase to at least one of the following: the first distillation column 100 and a sixth distillation column 130. The sixth distillation column 130 may receive the organic phase via a side inlet arrangement 138.

In an embodiment, the sixth distillation column 130 may recycle the aqueous phase via its top 134 back to at least one of the following: the first decanter 122 and the fifth distillation column 124. In this case, the aqueous phase comprises extractant-containing water.

When a higher furfural content is used in the process system than at the feed, it is worthwhile to recycle furfural. In this case, clean furfural, and not the mixture of furfural and water, is fed to the process system so that the amount of water does not increase in the process system.

Figure 2:
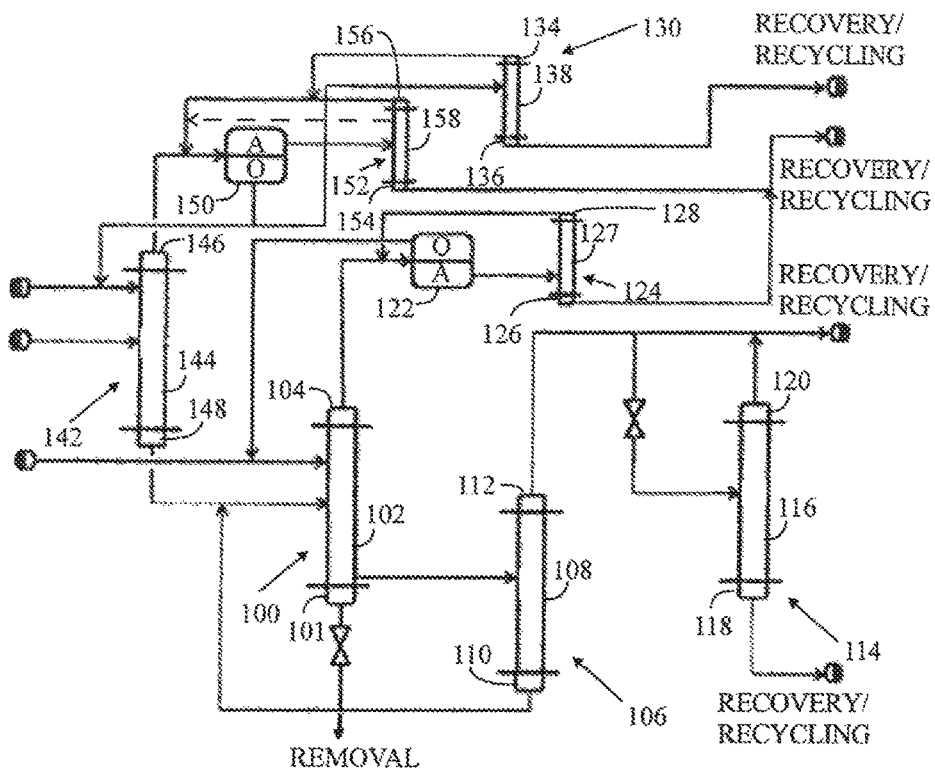
FIG. 2 shows an example of a process for separating chemical substances wherein furfural is also used.

In an embodiment shown in FIG. 2, the distillation column arrangement comprises a first distillation column 100 and a second distillation column 142. In this case, the second distillation column 142 may receive furfural, water and at least one mixture of an organic acid. The second distillation column 142 may receive these substances via its side arrangement 144. Furfural may be fed to the second distillation column 142 as make-up flow. In this case, too, the organic acid may be formic acid and/or acetic acid, for example.

On the basis of distillation, the second distillation column 142 may form a heterogeneous azeotrope of water and furfural at its top 146, which may be removed by the second distillation column 142 via its top 146 in order to separate the furfural from said at least one organic acid. With the furfural, water may also be removed. The azeotrope boils at a lower temperature than any other component in the second distillation column 142 and the azeotrope rises as distillate away from the second distillation column 142.

On the basis of azeotropic distillation, the second distillation column 142 may form said one or more organic acids and water on its bottom 148. The second distillation column 142 may feed said at least one organic acid from its bottom 148 to the first distillation column 100 in order to separate said at least one organic acid and furfural from one another. With one or more organic acids, water is passed from the second distillation column 142 to the first distillation column 100. Also in this case, which involves furfural, the process produces a mixed acid, water, furfural and an organic acid either to be reused in the process and/or to be sold as individual products.

In an embodiment, the at least one organic acid and water that are fed from the second distillation column 142 to the first distillation column 100 contain water 20 to 50% of the total mass or volume.

In an embodiment of FIG. 2, the arrangement comprises a third decanter 150. In this case, the second distillation column 142 may feed the furfural and water at its top 146 to the third decanter 150. The feed temperature of the aqueous furfural to the third decanter 150 may be about 20 to 95° C., for example. The feeding may be performed via the side arrangement 144 of the second distillation column 142. The third decanter 150 may separate the aqueous phase from the organic phase containing furfural. In the third decanter 150, the aqueous phase rises to the top and the organic phase, which is denser than water, remains at the bottom (the force causing acceleration being directed from the surface towards the bottom). The third decanter 150 may have a similar function as the second decanter 140. The third decanter 150 may feed at least part of the organic phase to at least one of the following: the second distillation column 142 and the sixth distillation column 130.

In an embodiment of FIG. 2, the purpose of the sixth distillation column 130 is to produce a pure furfural flow from the organic furfural-containing flow of the third decanter 150. The pure furfural may be obtained from the bottom 136 of the sixth distillation column 130. As side inlet or distillate of the sixth distillation column 130, a furfural-water flow may be obtained (which may be returned back to the decanter 150 in order to recover the residual furfural). Light components (impurities), which have possibly arrived with the feed, may be removed from the top 134 of the sixth distillation column 130.

The sixth distillation column 130 may thus receive the organic phase from the third decanter 150 and, by distillation, produce furfural contained in the organic phase on its bottom 136 for recovery and/or recycling. The reception may be performed via the side arrangement 138 of the sixth distillation column. The sixth distillation column 130 may produce, by distillation, purified furfural on its bottom 136.

In an embodiment of FIG. 2, the sixth distillation column 130 may feed the aqueous phase it has formed at its top 134 back to the third decanter 150. The aqueous phase at the top 134 contains furfural and water.

In an embodiment of FIG. 2, the arrangement comprises a seventh distillation column 152, the purpose of which is to separate water from the residual furfural and to produce a clean water flow to be returned to the fractionation process (away from the distillery). In this case, the third decanter 150 may feed the aqueous phase to the seventh distillation column 152, which may produce, by distillation, water on its bottom 154 for recovery and/or recycling. A clean water flow may be obtained from the bottom 154.

The seventh distillation column 152 may produce, by distillation, water and furfural at its top 156 and feed the water and furfural back to the third decanter 150. Instead of the top 156, the water and furfural may be transferred to the third decanter 150 via a side arrangement 158 of the seventh distillation column 152 (this transfer is shown by a broken line in FIG. 2). Especially in this case, light components (substances less dense than furfural), which may be impurities, may be removed from the top 156 of the seventh distillation column.

Example 1

Reaction of formic acid, acetic acid and hexanol. Acids and alcohol were introduced to a batch reactor in a proportion of 25 mol % of formic acid, 25 mol % of acidic acid and 50 mol % of hexanol. The test was carried out at a boiling point of the mixture at normal atmospheric pressure, and the reactor was provided with a full reflux condenser for returning the vaporizing components back to the reactor. Because the mixture boils in the test conditions, the reaction mixture is very well mixed up. Concentrations of the reaction mixture were monitored by taking samples as a function of time and analysing the samples with chromatographic methods. The test was continued for about 50 hours in order to make sure that no significant concentration changes happen in the reaction mixture any longer. It was assumed that esterification of the acids takes place in the reaction mixture, whereby hexyl formate is produced from the formic acids and hexyl acetate is produced from the acetic acid according to the following stoichiometry:

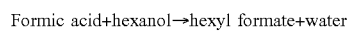
Formic acid+hexanol→hexyl formate+water

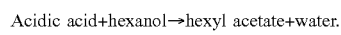
Acidic acid+hexanol→hexyl acetate+water.

The test confirmed that the acids do not react completely, but the reactions are reversible and equilibrium-limited. In the following, abbreviations according to Table 1 are used for the components of the reaction mixture.

TABLE 1

| Abbreviations for components of the reaction mixture | |
|---|---|
| Abbreviation | Component |
| A | Formic acid |
| B | Hexanol |
| C | Hexyl formate |
| D | Water |
| E | Acidic acid |
| F | Hexyl acetate |

Because the reactions are reversible, they are expressed as follows:

$$A+B \leftrightarrow C+D \qquad R_1$$

$$E+B \leftrightarrow F+D \qquad R_2$$

The reactions were provided with identifiers R1 and R2. Based on the test data obtained, the reaction-kinetic models could be formed for the reactions R1 and R2 to describe the behaviour of the reaction mixture as a function of concentration and temperature. A good match in relation to the test results was achieved by adapting the kinetic parameters ki of the progressing and reversible reaction models of the two-way reactions shown in table 2. In Table 2, rj represents the rate of a single reaction j, and Ci the concentration of a single component, where j is 1, −1, 2 or −2, and i is A, B, C, D, or E.

TABLE 2

Reaction-kinetic models

| Reversible total reaction | Progressing reaction | Reversible reaction |
|---|---|---|
| $R_1 = r_1 - r_{-1}$ | $r_1 = k_1 C_A C_B$ | $r_{-1} = k_{-1} C_C C_D$ |
| $R_2 = r_2 - r_{-2}$ | $r_2 = k_2 C_E C_B$ | $r_{-2} = k_{-2} C_F C_D$ |

Figure 3:
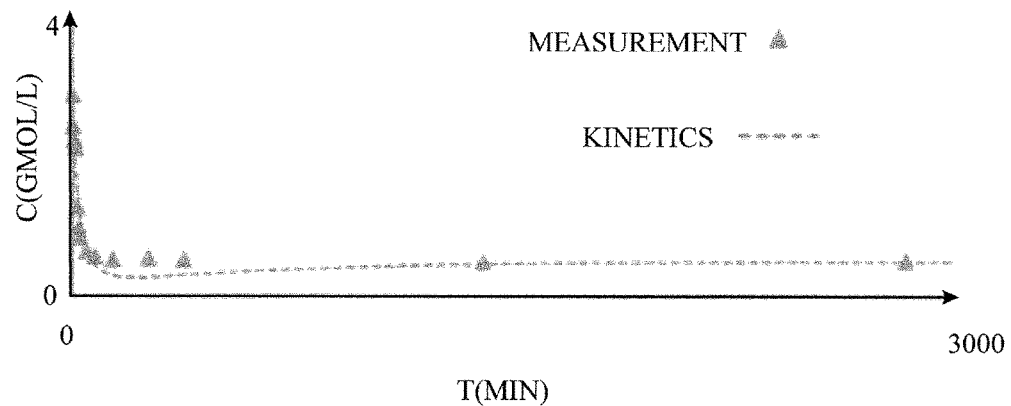
FIG. 3 shows an example of formation of hexyl formate under a first distillation condition.

FIG. 3 shows the original test data and concentration—time graphs predicted by the adapted kinetic model for formic acid under a certain distillation condition where the distillation column 100 has hexanol. In FIG. 3, the triangles represent measuring points and the dotted line kinetics according to the model. At first, the amount of formic acid is large, but it reacts with hexanol fast and soon ends up in a balance where there is a lot of ester and little of actual formic acid.

Figure 4:
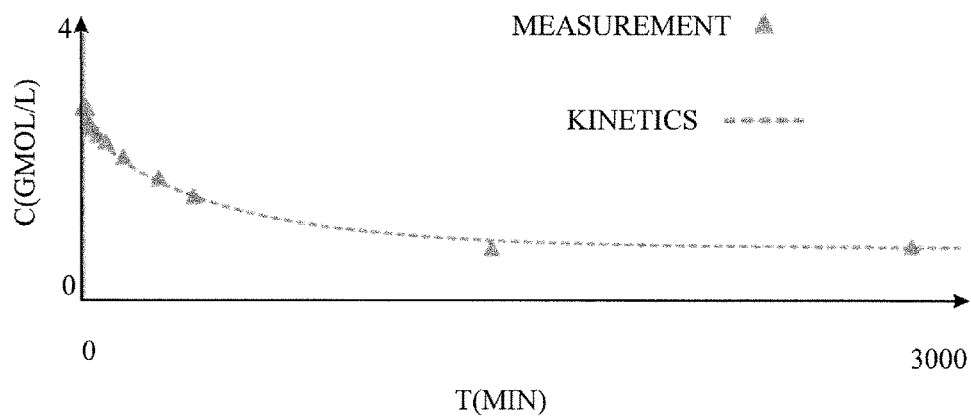
FIG. 4 shows an example of formation of hexyl acetate under a first distillation condition.

FIG. 4 shows the original test data and the concentration—time graphs predicted by the adapted kinetic model for acetic acid under a distillation condition in the distillation column 100 which contains hexanol. The triangles in FIG. 4 represent measuring points and the dotted line kinetics according to the model. At first, the amount of acetic acid is large, but it reacts with hexanol fast and soon ends up in a balance where there is a lot of ester and little of actual acetic acid.

Figure 5:
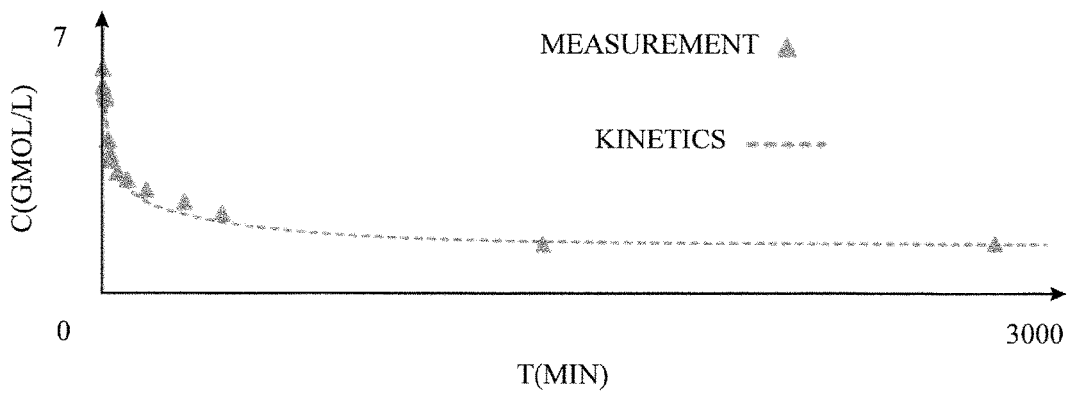
FIG. 5 shows an example of behaviour of an amount of hexanol in a first distillation column.

FIG. 5 shows the original test data and the concentration—time graphs predicted by the adapted kinetic model for hexanol under a distillation condition in the distillation column 100. The triangles in FIG. 5 represent measuring points and the dotted line kinetics according to the model. The amount of hexanol decreases fast and ends up in balance where most of the hexanol has reacted with organic acid, but some hexanol remains.

Figure 6:
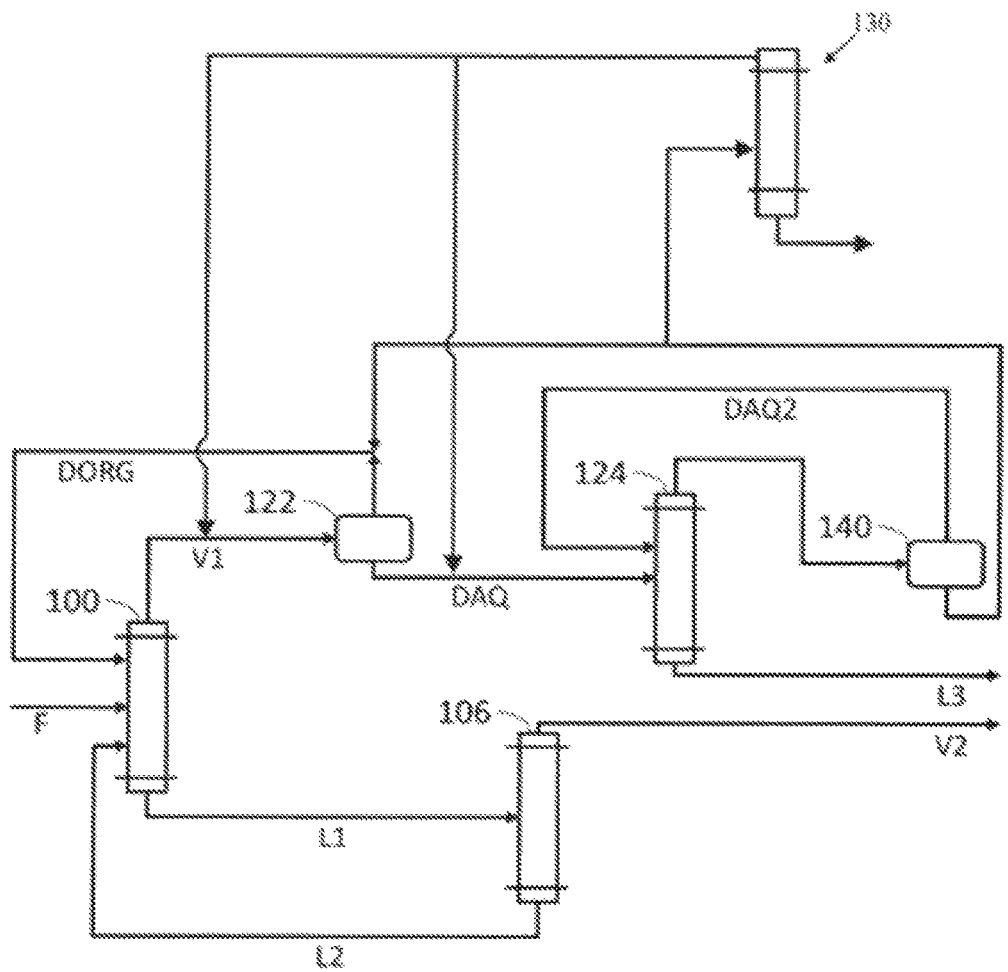
FIG. 6 shows a flow chart of the separation process according to Example 2.

Example 2, as shown by the flow chart of an abstraction process of FIG. 6, describes a heteroazeotropic extractive distillation. Heteroazeotropic extraction distillation was simulated by a commercial piece of software, taking into account the phase balance behaviour of a multicomponent mixture, and the kinetics of the chemical reactions taking place in the liquid phase. Mixture F, containing 40 percent by weight of water, 30 percent by weight of formic acid and 30 percent by weight of acetic acid, without restriction to these concentrations, is fed to a continuous distillation-based abstraction system. Hexanol is used in the system to advance water separation from the mixture F. The system consists of three distillation columns: water separation column 100, additive separation column 106, and water purification column 124. In addition, decanters 122 and 140 are used to separate the organic phase and water phase from each other. The organic steam DORG separated with a decanter is recycled to the water separation column, and the water stream DAQ separated with the decanter 122 is fed to the water purification column. The goal of the separation system is to separate the mixture F into a pure water stream L3 and concentrated acid stream V2. The stream L2 restores the additive back in the water separation column.

Hexanol is known to form a heteroazeotrope with water. The mixture according to the heteroazeotrope in question boils at a temperature that is lower than the boiling point of water. As a result, the hexanol-water-azeotrope leaves the top of the water removal column, and because the heteroazeotrope in question is the node boiling lowest in the mixture, the access of acids into the distillate stream may be prevented. The obtained distillate stream forms, as it condenses, two liquid phases whereby by decanting an aqueous stream DAQ and an organic stream are obtained. As shown in example 1, hexanol reacts with formic acid and acetic acid, forming hexyl formate and hexyl acetate.

TABLE 3

Composition of the streams as components' percentage by weight.

| | F | V1 | L1 | V2 | L2 | DORG | DAQ | DAQ2 | L3 |
|---|---|---|---|---|---|---|---|---|---|
| Water | 46 | 62 | 1 | 6 | 0 | 7 | 99 | 78 | 100 |
| Formic acid | 27 | 0 | 8 | 47 | 0 | 0 | 0 | 0 | 0 |
| Acetic acid | 27 | 0 | 23 | 47 | 0 | 0 | 0 | 0 | 0 |
| Hexanol | 0 | 15 | 5 | 0 | 0 | 36 | 1 | 22 | 0 |
| Hexyl formate | 0 | 0 | 26 | 0 | 14 | 0 | 0 | 0 | 0 |
| Hexyl acetate | 0 | 23 | 37 | 0 | 86 | 57 | 0 | 0 | 0 |

A dynamic balance refers to a steady state where the space divisions and temperatures according to the concentrations at different parts of the processes stabilise. The separation system which at its initial stage only had hexanol, formic acid, acetic acid, and water was allowed to set at the steady state. Suddenly, it was noted that the chemical reactions taking place do not prevent the reaching of the separation goal in question, but make it more advantageous. The hexyl formate and hexyl acetated that were formed behave in the separation system similarly to hexanol, and water separation and concentration of acids may be implemented by the separation process in question. Stream compositions according to the steady state are shown in Table 3.

As a summary, it may be noted that there are in use at least two organic acids that are at least formic acid and acetic acid. Of these, formic acid catalyses (powerful acid catalysis) the formation of esters from extractants, and the generation of esters in the mixture is inevitable. Acetic acid, on the other hand, is a weak acid and does not produce strong acid catalytic conditions.

To be more precise, formic acid forms strong acid-catalysed conditions in several parts of the column 100 and, as a result, the extractants used form a major amount of esters in the distillation system. Separation of formic acid and acetic acid in the system is possible when esters of both acids are formed in the column 100. So, the separation of a formate from a product acid is not possible without the presence of an acetic acid ester, that is, the separation of organic acids is based on esters formed with both extractants and acid catalytic conditions formed by formic acid.

The extractant component forms a heterogeneous azeotrope with water (minimum azeotrope). In such a case, the extractant forms an azeotrope under specific conditions (under 100° C.). The extractant (hexanol, 2-methyl pentanol) is a heavier component than acetic acid, water, and formic acid (and a mixture of acetic acid and formic acid) for their separation to be possible at later stages.

The minimum azeotrope allows water to rise up in the column and become separated from the acids. The heteroazeotrope, in turn, has an effect on that the components are decantable.

In recycling solutions, it is possible to push the acetate forming reactions into balance, and therefore, in a steady state situation, the system acts as a concentration and separation system of the mixture acid, which if need be also allows the production of ester products. If the extractants are alcohols, they react into esters in the column 100.

Figure 7:
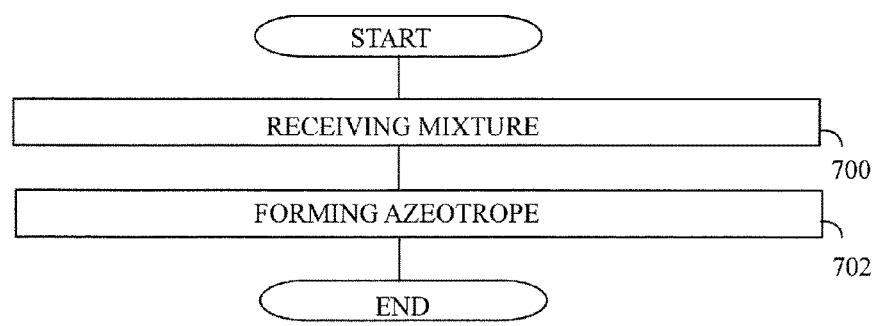
FIG. 7 shows an exemplary flow chart of a method.

In FIG. 7, and example of a chemicals separation method is shown. At step 700, the first distillation column 100 receives a mixture comprising water and at least one organic acid, and at least one extractant which comprises at least one of the following: hexanol, an ester of hexanol with said at least one organic acid and 2-methylpentanol. At step 702, a heterogeneous azeotrope of water and extractant is formed by said first distillation column 100 at the top 104 of the first distillation column 100, based on extraction distillation, said first distillation column 100 removing the azeotrope through its top 104 in order to separate water from organic acid.

Even though the invention has been described above with reference to the examples according to the accompanying drawings, it is clear that the invention is not restricted thereto but may be modified in many ways within the scope of the accompanying claims.

The invention claimed is:

1. A process system for separating chemicals, said system comprising:
   a first distillation column (100) having a top (104),
   a first decanter (122) having a top and a bottom, and
   a third distillation column (106) having a top (112) and a bottom (110),
   wherein:
      said first distillation column (100) is configured to operate in a pressure range at or below 1 bar and receive a mixture that comprises water and at least two organic acids including formic acid and acetic acid, and an extractant that comprises at least one of the following: hexanol, an ester of hexanol with at least two organic acids, and 2-methylpentanol;
      said first distillation column (100) is configured to form a heterogeneous azeotrope of water and extractant at said top (104) on the basis of reactive heteroazeotropic extractive distillation and without controlling chemical reactions of the extractant and said at least two organic acids, wherein said first distillation column (100) is configured to remove said heterogeneous azeotrope of water and extractant through said top (104) into the first decanter (122) to separate water from said at least two organic acids;
      said decanter (122) is configured to separate the heterogeneous azeotrope of water and extractant into an organic phase comprising: the extractant which, as a substance less dense than water, rises to said top of the decanter (122), and an aqueous phase which, with a greater density than the organic phase, remains at said bottom of the decanter (122);
      said first distillation column (100) is configured to feed said at least two organic acids, extractant and water to the third distillation column (106); and
      said third distillation column (106) is configured to form extractant at said bottom (110) for at least one of recovery or recycling, and the third distillation column (106) is configured to form, based on distillation, a mixture of water and said at least two organic acids at said top (112) for at least one of recovery or recycling.

2. A process system as claimed in claim 1, wherein the process system further comprises a fourth distillation column (114) configured to receive said mixture of water and said at least two organic acids coming from the top (112) of the third distillation column (106), the fourth distillation column (114) being further configured to form by distillation at its bottom (118) at least one concentrated organic acid of said at least two organic acids for at least one of recovery or recycling, and the fourth distillation column (114) being configured to form at its top (120) a mixture of water and said at least one concentrated organic acid for at least one of recovery or recycling.

3. A process system as claimed in claim 1, wherein the first distillation column (100) is configured to receive furfural as extractant, and said first distillation column (100) is configured to remove the furfural through said top (104).

4. A process system as claimed in claim 1, wherein the first distillation column (100) is configured to feed the heterogeneous azeotrope of water and extractant of said top (104) to the first decanter (122) which is configured to separate from each other the aqueous phase and organic phase that comprises extractant, and to feed at least part of the organic phase back to the first distillation column (100).

5. A process system as claimed in claim 4, wherein the process system comprises a fifth distillation column (124), and the first decanter (122) is configured to feed the aqueous phase to the a fifth distillation column (124) which is configured to form, by distillation, water at a bottom (126) of the fifth distillation column (124) for at least one of recovery or recycling.

6. A process system as claimed in claim 5, wherein the fifth distillation column (124) is configured to form, by distillation, extractant and water at a top (128) of the fourth distillation column (124) and to feed the extractant and the water to a fifth decanter (140), which is configured to separate from each other an aqueous phase and organic phase which contains extractant, and to feed the aqueous phase back to the fifth distillation column (124), and the organic phase from the fifth decanter (14) to at least one of the following: the first distillation column (100) or a sixth distillation column (130).

7. A process system as claimed in claim 6, wherein the sixth distillation column (130) is configured to recycle the extractant containing water through a top (134) of the sixth distillation column (130) and to at least one of the following: the first decanter (122) or the fifth distillation column (124).

8. A distillation column arrangement comprising:
   a first distillation column (100) having a top (104),
   a second distillation column (142) having a top (146) and a bottom (148),
   a first decanter (122) having a top and a bottom, and
   a third distillation column (106) having a top (112) and a bottom (110),
   wherein:
      the first distillation column (100) being configured to operate in a pressure range at or below 1 bar and receive a mixture that comprises water and at least two organic acids including formic acid and acetic acid, and an extractant that comprises at least one of the following: hexanol, an ester of hexanol with at least two organic acids and 2-methylpentanol,
      said first distillation column (100) is configured to form a heterogeneous azeotrope of water and extractant at said top (104) on the basis of reactive heteroazeotropic extractive distillation and without controlling chemical reactions of the extractant and said at least two organic acids, wherein said first distillation column (100) is configured to remove said heterogeneous azeotrope of water and extractant through said top (104) into the first decanter (122) for separating water from said at least two organic acids;
      said first decanter (122) is configured to separate the heterogeneous azeotrope of water and extractant into an organic phase comprising the extractant which, as a substance less dense than water, rises to said top of the decanter (122), and an aqueous phase which, with a greater density than the organic phase, remains at said bottom of the decanter (122);

said first distillation column (100) is configured to feed a portion of said at least two organic acids, extractant and water to the third distillation column (106);

said third distillation column (106) is configured to form extractant at said bottom (110) for at least one of recovery or recycling, and the third distillation column (106) is configured to form, based on distillation, a mixture of water and said at least two organic acids at said top (112) for at least one of recovery or recycling;

said second distillation column (142) is configured to receive furfural and a mixture of water and said at least two organic acids; and said second distillation column (142) is configured to:
form a heterogeneous azeotrope of water and furfural at said top (146) on the basis of heteroazeotropic distillation, wherein said second distillation column (142) is configured to remove through said top (146) for separating furfural from said at least two organic acids;
form said at least two organic acids and water at said bottom (148) on the basis of heteroazeotropic distillation; and
feed said at least two organic acids and water from the bottom (148) of said second distillation column (142) to the first distillation column (100) for separating said at least two organic acids and the furfural from one another.

9. An arrangement as claimed in claim 8, wherein said at least two organic acids and the water to be fed into the first distillation column (100) contain 20 to 50% of water.

10. An arrangement as claimed in claim 8, wherein the arrangement comprises a third decanter (150), and the second distillation column (142) is configured to feed the furfural and water from its top (146) to the third decanter (150), which is configured to separate an aqueous phase from an organic phase that contains furfural and to feed the organic phase to at least one of the following: the second distillation column (142) or a sixth distillation column (130).

11. An arrangement as claimed in claim 10, wherein the sixth distillation column (130) is configured to receive the organic phase from the third decanter (150) and to form furfural at a bottom (136) of the sixth distillation column (130) for at least one of recovery or recycling.

12. An arrangement as claimed in claim 11, wherein the sixth distillation column (130) is configured to form furfural at the bottom thereof by distillation for at least one of recovery or recycling and to feed an aqueous phase it formed at its top (134) back to the third decanter (150).

13. An arrangement as claimed in claim 10, wherein the arrangement comprises a seventh distillation column (152), and the third decanter (150) is configured to feed the aqueous phase to the seventh distillation column (152) which is configured to form water at a bottom (154) of the seventh distillation column (152) by distillation for at least one of recovery or recycling, and the seventh distillation column (152) is configured to form aqueous furfural by distillation at a top (156) of the seventh distillation column (152) or for transfer by a side arrangement (156) of the seventh distillation column (152) and to feed the aqueous furfural to the third decanter (150).

14. A method for separating chemicals, said method comprising the steps of:
receiving (700) in a first distillation column (100), which operates in a pressure range at or below 1 bar, a mixture that comprises water and at least two organic acids including formic acid and acetic acid, and an extractant that comprises at least one of the following: hexanol, an ester of hexanol with at least two organic acids and 2-methylpentanol;

forming (702) in said first distillation column (100) a heterogeneous azeotrope of water and extractant at a top (104) of the first distillation column (100) on the basis of reactive heteroazeotropic extractive distillation, wherein said first distillation column (100) removes said heterogeneous azeotrope of water and extractant through said top (104) to a first decanter (122) for separating water from said at least two organic acids;

separating in the first decanter (122) the heterogeneous azeotrope of water and extractant into an organic phase comprising the extractant which, as a substance less dense than water, rises to a top of the decanter (122), and an aqueous phase which, with a greater density than the organic phase, remains at a bottom of the decanter (122);

feeding a portion of said at least two organic acids, extractant and water from the first distillation column (100) to a third distillation column (106); and forming extractant at a bottom (110) of said third distillation column (106) for at least one of recovery or recycling, and forming a mixture of water and said at least two organic acids by distillation at a top (112) of the third distillation column (106) for at least one of recovery or recycling.

15. A method as claimed in claim 14, wherein the relative amount of acetic acid in the at least two organic acids is 10% or more.

16. A method as claimed in claim 14, further comprising the steps of:
receiving in a fourth distillation column (114) the mixture of water and said at least two organic acids coming from the top (112) of the third distillation column (106),
forming at least one concentrated organic acid of said at least two organic acids by distillation in a fourth distillation column (114) at a bottom (118) of the fourth distillation column (114) for at least one of recovery or recycling, and
forming a mixture of water and said at least one concentrated organic acid in the fourth distillation column (114) at a top (120) of the fourth distillation column (114) for at least one of recovery or recycling.

17. A method as claimed in claim 14, further comprising the steps of:
receiving in the first distillation column (100) also furfural as extractant, and
removing the furfural from said first distillation column (100) through the top (104).

18. A method as claimed in claim 14, further comprising the steps of:
feeding with the first distillation column (100) the heterogeneous azeotrope of water and extractant from said top (104) to the first decanter (122),
separating in the first decanter (122) an aqueous phase and an organic phase that contains extractant from one another, and
feeding at least part of the organic phase back to the first distillation column (100).

19. A method as claimed in claim 18, further comprising the steps of:
feeding the aqueous phase from the first decanter (122) to a fifth distillation column (124), and forming water by distillation at the bottom (126) of the fifth distillation column (124) for at least one of recovery or recycling.

20. A method as claimed in claim 19, further comprising the steps of:
    forming in the fifth distillation column (124) extractant at the top (128) of the fifth distillation column (124) and feeding the extractant to the second decanter (140),
    separating an aqueous phase and an organic phase that contains extractant from one another in the second decanter (140), and
    feeding the aqueous phase from the second decanter (140) back to the fifth distillation column (124) and the organic phase from the second decanter (140) to at least one of the following: the first distillation column (100) or a sixth distillation column (130).

21. A method as claimed in claim 20, further comprising the step of recycling the water that contains extractant with the sixth distillation column (130) through the top (134) of the sixth distillation column (130) back to at least one of the following: the first decanter (122) or the fifth distillation column (124).

22. A method as claimed in claim 14, further comprising the steps of:
    receiving in a second distillation column (142) furfural and a mixture of water and said at least two organic acids;
    forming in the second distillation column (142) a heterogeneous azeotrope of water and furfural at the top (146) of the second distillation column (142) on the basis of heteroazeotropic distillation, removing the heterogeneous azeotrope of water and furfural from said second distillation column (142) through the top (146) thereof for separating furfural from said at least two organic acids;
    forming said at least two organic acids and water at a bottom (148) of the second distillation column (142) on the basis of the heteroazeotropic distillation; and
    feeding said at least two organic acids and water from the bottom (148) of said second distillation column (142) to said first distillation column (100) for separating said at least two organic acids and furfural from one another.

23. A method as claimed in claim 22, wherein the at least two organic acids and water to be fed to the first distillation column (100) contain 20 to 50% of water.

24. A method as claimed in claim 22, further comprising the steps of:
    feeding aqueous furfural from the top (146) of the second distillation column (142) to the third decanter (150),
    separating an aqueous phase from an organic phase that contains furfural, and
    feeding the organic phase to at least one of the following: the second distillation column (142) and a sixth distillation column (130).

25. A method as claimed in claim 24, further comprising the step of receiving in the sixth distillation column (130) the organic phase from the third decanter (150) and forming furfural at the bottom (136) of the sixth distillation column (130) for at least one of recovery or recycling.

26. A method as claimed in claim 25, further comprising the step of forming an aqueous phase at the top (134) of the sixth distillation column (130) and feeding the aqueous phase back to the third decanter (150).

27. A method as claimed in claim 26, further comprising the steps of:
    feeding the aqueous phase from the third decanter (150) to a seventh distillation column (152),
    forming water by distillation at a bottom (154) of the seventh distillation column (152) for at least one of recovery or recycling and water that contains furfural at a top (156) or for transfer by a side arrangement (156) of the seventh distillation column (152), and
    feeding the water that contains furfural that contains water from the top (156) to the third decanter (150).

\* \* \* \* \*